United States Patent [19]

Calzada Badia et al.

[11] 4,379,793

[45] Apr. 12, 1983

[54] PROCESS FOR SYNTHESIS OF ESTERS OF N-(4'-HYDROXYPHENYL)ACETAMIDE WITH DERIVATIVES OF 5-BENZOIL-1-METHYL PYRROLE-2-ACETIC ACIDS

[75] Inventors: Jose-Maria Calzada Badia; Antonio Boleda Vila; Jose Sabater Sanmartin; Maria J. Villazon Meneses, all of Barcelona, Spain

[73] Assignee: Calzada y Cia, S.R.C., Barcelona, Spain

[21] Appl. No.: 285,341

[22] Filed: Jul. 20, 1981

[30] Foreign Application Priority Data

Nov. 11, 1980 [ES] Spain ..................................... 497.136

[51] Int. Cl.$^3$ ..................... A61K 31/40; C07D 207/09
[52] U.S. Cl. ..................................... 424/274; 548/539
[58] Field of Search ...................... 260/326.46, 326.47; 424/274; 548/539

[56] References Cited

U.S. PATENT DOCUMENTS 4,187,230  2/1980  Wiegand et al. ............... 260/326.47

Primary Examiner—Richard Raymond
Attorney, Agent, or Firm—Cushman, Darby & Cushman

[57] ABSTRACT

4'-acetamidophenyl-2-(5'-p-toluyl-1'-methylpyrrole-)acetate and related compounds exhibiting anti-inflammatory, analgesic and antipyretic activity are disclosed.

3 Claims, No Drawings

PROCESS FOR SYNTHESIS OF ESTERS OF N-(4'-HYDROXYPHENYL)ACETAMIDE WITH DERIVATIVES OF 5-BENZOIL-1-METHYL PYRROLE-2-ACETIC ACIDS

The present invention relates to a method for the synthesis of esters of N-(4'-hydroxyphenyl)acetamide with 5-benzoil-1-methylpyrrole-2-acetic acids, through which compounds are obtained with the following general formula:

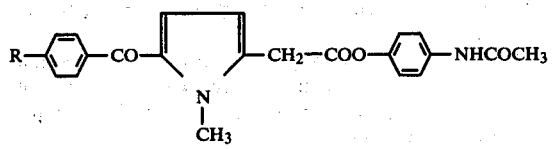

in which R is an alkyl group of 1 to 4 carbon atoms, either linear or branched chain, or represents a halogen, the compounds so produced and to pharmaceutical compositions containing such compounds.

The compounds of general formula (I) include all of the optically active forms and possible racemic mixtures of the compounds as well.

The compounds of the inventive exhibit anti-inflammatory, analgesic and antipyretic activities, all of which are therapeutic interest. Methods directed to treating such symptoms are also disclosed. They can be formulated in pharmaceutical compositions for oral and rectal administration, which contain them as active ingredients, together with suitable diluents or solvents. Orally, they can be administered in the form of capsules, tablets, dragees, solutions, suspensions, syrups and emulsions, and rectally, as suppositories. The administration doses of the active principles can vary within wide limits, depending on the desired therapeutic activity.

The compounds herein described are compounds of the desired two pharmacologically active molecules, one of which is an alcohol, such as N-(4'-hydroxyphenyl)acetamide, with an analgesic-type action, and the other molecule is an acid, such as 5-benzoil-1-methylpyrrole-2-acetic, with strong anti-inflammatory action. When these compounds are administered orally, the medicine is absorbed as such, reaching the blood stream intact, where it is distributed then metabolized through the action of plasmatic stearases into the compound's acid and alcohol components, each performing their therapeutical action.

Among the compounds obtained through the synthesis procedure of the present invention, 4'-acetamidophenyl-2-(5'-p-toluyl-1'-methylpyrrole)acetate and 4'-acetamidophenyl-2-(5'-p-chlorobenzoil-1'-methylpyrrole)acetate are of the greatest therapeutic interest.

In essence, the method referred to in the present invention is characterized in that the acyl halogenide is obtained from 5-benzoil-1-methylpyrrole-2-acetic acids, according to the general synthesis method, through the reaction of these acids with a halide or a phosphorus or sulfur oxyhalide, and subsequently this acyl halogenide is reacted with N-(4'-hydroxyphenyl)acetamide, yielding a compound with the following general formula:

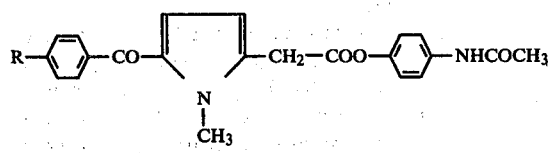

in which R is a $C_1$-$C_4$ straight or branched alkyl group or R represents a halogen, preferably fluorine or chlorine.

The general method for the synthesis of esters of formula type (I), the object of the present invention, is indicated in the following general reaction diagram:

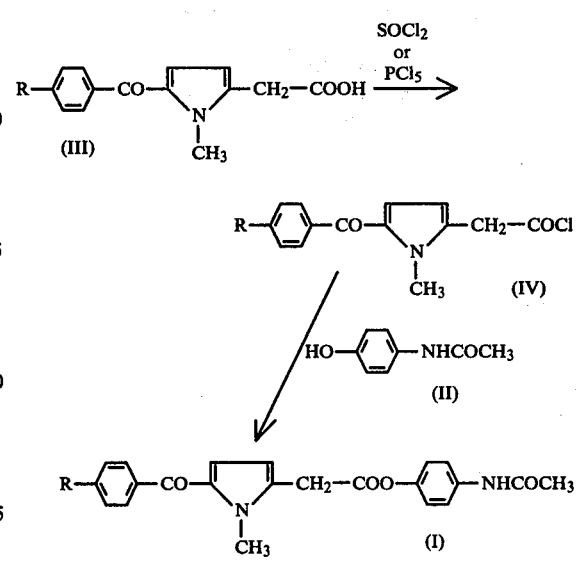

Consequently, the general synthesis method includes obtaining acyl halogenide (IV) from compounds having the general formula (III) and subsequent treatment with alcohol (II) to obtain the compound (I).

The intermediate compound (IV) is obtained from the initial acid form (III), according to general acyl halogenide synthesis methods, using either $SO\ Cl_2$ or $PCl_5$ in an anhydrous medium. It can also be obtained in the respective acyl halogenide of (III), by reaction in an anhydrous organic solvent medium with $PBr_3$.

Subsequently, the interaction of the acyl halogenide (IV) with the alcohol (III) in a suitable anhydrous organic solvent, provides the desired general formula compound (I).

To assist understanding of the disclosed process, an example is given below of the method used to obtain the compound 4'-acetamidephenyl-2-(5'-p-toluyl-1'-methylpyrol)acetate, it being understood that by following similar methods other compounds included within general formula (I) are obtained.

EXAMPLE (a) Synthesis of 2-(5'-p-toluyl-1'-methylpyrol)acetyl chloride.

Dissolve 12 g of 5-p-toluyl-1'-methyl-pyrol-acetic acid in 100 ml. of chloroform. Add 5 ml. of $SO\ Cl_2$ and keep under reflux for 24 hours. Vacuum distil the chloroform and add 100 ml. of toluene, then distilling again. The residue is a dark thick oil, and is acyl chloride, which is used without purifying in the following step.

(b) Synthesis of 4'-acetamidophenyl-2-(5'-p-toluyl-1'-methyl-pyrol)acetate.

Dissolve the previous residue in 250 ml. of hexane and add a solution of 7 g of N-(4'-hydroxyphenyl) acetamide very slowly to it, dissolved in 20 ml. of piridine. Shake at room temperature for 24 hours. Acidulate with HCl 1 N to $pH_2$ and the product sought is suspended between the aqueous layer and the organic layer. Collect the product through filtration, washing it with hexane. 10 g of product are obtained, whose melting point is 210° C., by thin-layer chromatography on Kiesegel Merck F 254; the developing solvent was chloroform/acetic acid (19:1), causing a single strain, whose Rf is 0.43.

The analysis calculated for the $C_{23} H_{22} N_2 O_4$ is as follows:

C: 70.77%; H: 5.64%; $N_2$: 7.18%; O: 16.41%.

In the compound obtained, we find C: 70.70%; H: 5.61%; N: 7.00%; O: 16.39%.

What is claimed is:

1. A compound of the formula:

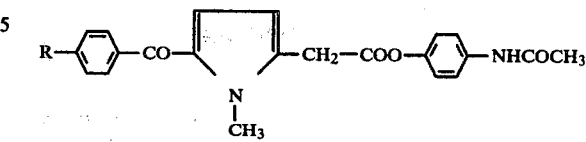

wherein R is a $C_1$–$C_4$ alkyl group or a halogen atom and the pharmaceutically acceptable salts thereof.

2. A compound 4'-acetamidophenyl-2-(5'-p-toluyl-1'-methyl-pyrrole) acetate and the pharmaceutically acceptable salts thereof.

3. An anti-inflammatory pharmaceutical composition containing as the active ingredient the compound of claim 1 or 2 together with a pharmaceutically acceptable carrier or diluent.